United States Patent [19]
Darrah

[11] Patent Number: 5,199,056
[45] Date of Patent: Mar. 30, 1993

[54] MAMMOGRAPHY COMPRESSION PADDLE

[76] Inventor: Carol J. Darrah, 8100 E. 22nd St. N., Wichita, Kans. 67226

[21] Appl. No.: 441,996

[22] Filed: Nov. 28, 1989

[51] Int. Cl.⁵ ............................................. A61B 6/04
[52] U.S. Cl. ...................................... 378/37; 378/208
[58] Field of Search .............. 378/37, 207, 208, 210, 378/177, 180, 20, 195

[56] References Cited

U.S. PATENT DOCUMENTS

| | | | |
|---|---|---|---|
| 4,573,180 | 2/1986 | Summ | 378/180 |
| 4,905,269 | 2/1990 | Mosby | 378/37 |
| 4,943,986 | 7/1990 | Barbarisi | 378/37 |

FOREIGN PATENT DOCUMENTS 0403400 10/1973 U.S.S.R. ................................. 378/37

Primary Examiner—Janice A. Howell
Assistant Examiner—Don Wong
Attorney, Agent, or Firm—Edward L. Brown, Jr.

[57] ABSTRACT

The present invention provides a mammographic compression technique which permits the paddle to be aligned in any angular view with the cutout portion of the paddle positioned over the implant to reduce the amount of compression of the implant thereby lessening the blockage of the breast tissue. The invention comprises a compression paddle formed of x-ray transmissive material having sidewalls extending normally from a planar bottom surrounding the periphery which lays outside of the cutout portion.

6 Claims, 2 Drawing Sheets

MAMMOGRAPHY COMPRESSION PADDLE

FIELD OF THE INVENTION

The invention relates to mammography and more specifically to mammography patients with breast implants.

DISCUSSION OF PRIOR ART

Mammography involves compressing the breast tissue between a pair of plates, one of which can be moved toward or away from the other, while an X-ray is taken of the breast tissue for detecting internal growths including tumors, cancer and other types of defects or abnormalities. The radiographic examination, also referred to as a mammogram, has become widely used in the past two decades on adult females as a diagnostic tool. In prior art procedures the amount of radiation exposure to certain patients has been substantially greater due to the multiple angular positions that are X-rayed and the difficulty of compressing the breast tissue as a result of the implant.

A patient having a breast implant is more difficult to X-ray because that portion of the implant which overlays the breast tissue in the X-ray picture blocks out the breast tissue and only a portion of the breast tissue can be viewed. The breast implant material is pliable and soft when the breast is placed under compression, the implant will also spread out and block substantial portions of breast tissue from being viewed in a single view. With only a portion of the breast tissue visible with implant patients, radiologists have resorted to numerous multiple angular views so as to better view the blocked tissue with the obvious disadvantage of increased radiation exposure to the patient. Also when compression is applied over the implant, the spreading of the implant compacts the anterior portion of the breast between the implant and the skin. This reverses the desired results of compressing breast tissue which is to spread the tissue and make it uniformly thinner. Radiation exposure is increased when the breast tissue cannot be adequately compressed because of the pressure of the implant.

Various prior art patents involving mammography compression paddles are illustrated in the following patents.

(1) U.S. Pat. No. 3,578,971 Lasky
(2) U.S. Pat. No. 3,971,950 Evans, et al.
(3) U.S. Pat. No. 4,090,084 Epstein, et al.
(4) U.S. Pat. No. 4,599,738 Panetta, et al.

None of the prior art patents listed above are concerned with the problems created with implant patients. The only known procedure other than the present invention in dealing with the implant patient is the technique of compressing only the outer more anterior portions of the breast so as not to compress the implant and block more of the breast tissue. The obvious disadvantage of this technique is that it does not allow the radiologist to see the tissue portions of the breast more inwardly spaced near the chest wall. In single X-ray pictures this prior art implant technique severely restricts the amount of breast tissue that could be viewed in a single film, thus requiring additional pictures at different angles in order to see the entire breast.

SUMMARY OF THE INVENTION

The present invention provides a mammographic compression technique which permits the paddle to be aligned in any angular view with the cutout portion of the paddle positioned over the implant so that there is less compression of the implant with accordingly less blockage of breast tissue since the implant is not caused to widely spread as it would under conventional paddles. The cutout paddle permits larger areas of tissue closer to the chest wall to be viewed in a single X-ray picture. The paddle with its cutout areas surrounding the implant minimizes the lateral flattening of the implant while increased areas of compressed breast tissue are viewable.

The principal object of the present invention is to provide a compression paddle for implant mammography patients which maximizes the breast tissue viewable in an X-ray photo.

Another object of the present invention is the utilization of a compression technique in mammography which, while compressing the breast tissue, does not compress or spread a breast implant.

Other further objects and advantages of the invention will become apparent from consideration of the following specifications taken in conjunction with the drawings in which.

DESCRIPTION OF THE PREFERRED EMBODIMENT

Figure 1:
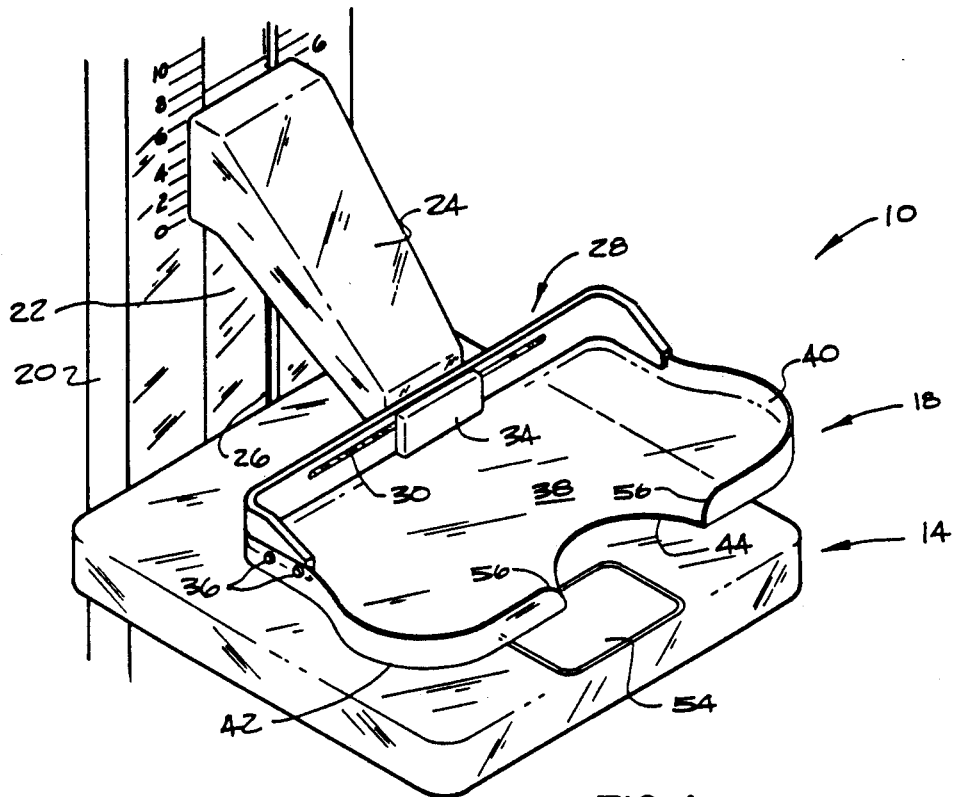
FIG. 1 is a perspective view of the paddle of the present invention on conventional mammography apparatus, with portions of the apparatus not shown.

Referring to the drawings and more particularly to FIG. 1, a mammography system is generally illustrated by reference numeral 10. The system 10 which is generally known in the prior art, includes an X-ray source 12 (FIG. 2) positioned over a stationary member 14 and a movable compression paddle 18 positioned therebetween. Located within stationary member 14 is an X-ray film plate 16, as symbolically illustrated in FIGS. 2 and 3. The film plate 16 can also be positioned on top of member 14, as seen in FIG. 1, with the photo timer 54 positioned thereunder. Photo timer 54 controls the amount of exposure to the film plate.

Figure 3:
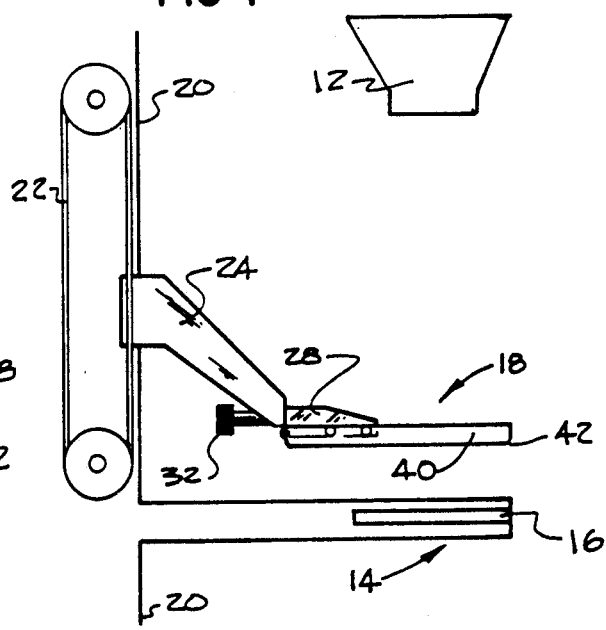
FIG. 3 is a side elevational view of the compression paddle of the present invention with some portions of the apparatus shown symbolically.
Figure 4:
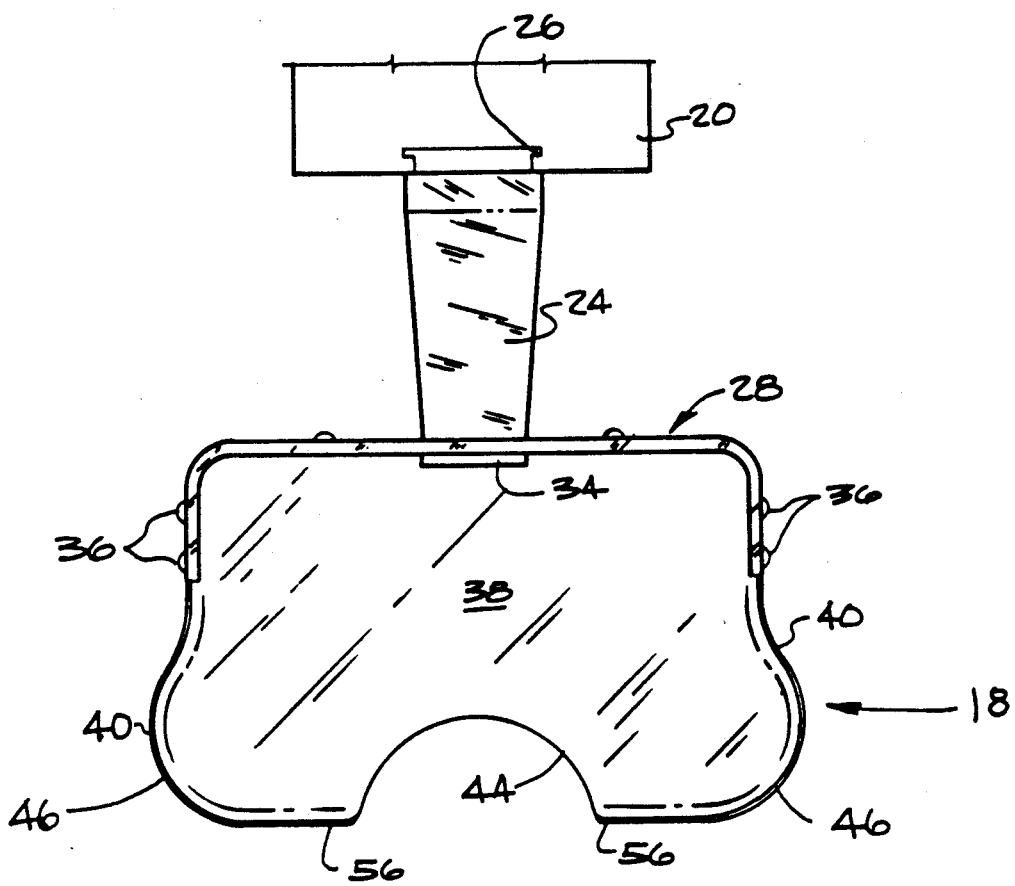
FIG. 4 is a top plan view of the compression paddle of the present invention and its connecting support arm.

Movable paddle 18 is mounted on a support arm 24 by way of a support bracket 28. Bracket 28 attaches to paddle 18 through a series of attachment screws 36. Paddle 18 can be moved laterally on its support arm 24 by releasing mounting bolt 32 as seen in FIG. 3. Bolt 32 attaches to plate 34 and when drawn tight prevents the paddle 18 from sliding laterally with bolt 32 in a longitudinal slot 30 in the support bracket. Support arm 24 moves up and down in a recessed track 26 as best seen in FIG. 4. The movement of support arm 24 is caused by a linear transport belt 22, symbolically shown in FIG. 3, which attaches to arm 24. Transport belt 22 is driven in either direction manually or by an electric motor not shown or any equivalent driving device well known in the art. When transport belt 22 is lowering paddle 18 in compression of the breast tissue of the patient, the system will be controlled by some pressure sensing apparatus which will prevent the system from exceeding certain preset pressure limits.

The movable paddle 18 is constructed of a transparent polycarbonate, such as non-fire retardant Lexan, and is approximately 0.100 inches in thickness. The polycarbonate material is radiation or X-ray transmissive so as not to block the X-ray beam which is transmitted from above by source 12. The paddle 18 is also transparent to the human eye to allow the technologist who is performing the mammogram to visually confirm the position of the breast prior to the exposure, insuring maximum compression and eliminating any possible skin folds which might distort the film image. Paddle 18 is tray-like in appearance, having a planar bottom 38 and a circumferential side wall 40 extending around the periphery thereof with the exception of the cutout area 44 located on the front edge of the paddle. The front corners 46 of the paddle extend longitudinally, as viewed in FIG. 4, to give the technologist increased paddle width which is desirable with certain patients when taking a lateral view picture. The ends 56 of the side wall 40 adjacent to cutout 44 are shaped with a corner radius, as best seen in FIG. 1, so as not to provide any sharp corners. Likewise, the juncture between the side wall 40 and the bottom 38 of the paddle is shaped with a radius 42 so as not to provide a sharp edge. The cutout 44 is arcuate in shape with a substantially constant radius which is shaped slightly smaller than the horizontal cross section of a typical breast implant in place. If the patient being X-rayed has a substantially larger or smaller implant, a different paddle can be utilized having a cutout shaped in closer proximity to the implants horizontal cross section.

Figure 5:
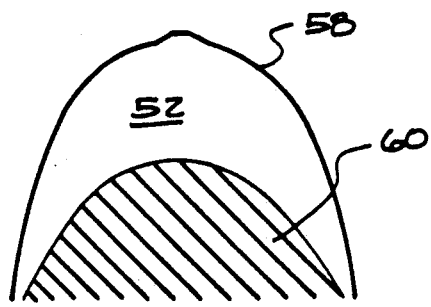
FIG. 5 is a symbolic view of an X-ray film in the craniocaudal view of a breast implant patient utilizing a prior art paddle.

The prior art paddles without the cutout, produce an X-ray image such as is symbolically shown in FIG. 5. The outline of the breast tissue is illustrated by line 58 and area 60 illustrates the compressed implant which blocks substantial areas of breast tissue 52. Also the compression thickness of the breast tissue is generally thicker with with an implant than in the absence of an implant.

OPERATION OF PRESENT INVENTION

Figure 2:
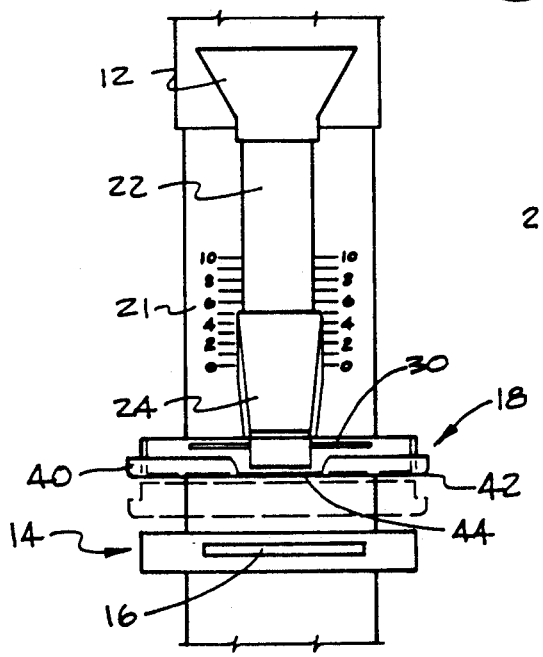
FIG. 2 is a front elevational view of the compression paddle and its adjacent apparatus, some of which is symbolically shown.
Figure 6:
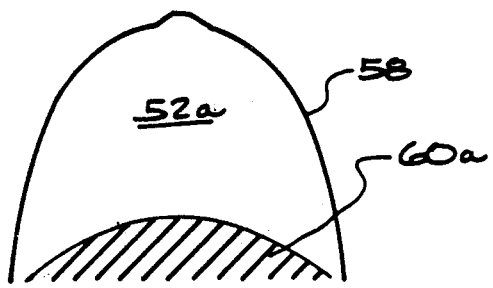
FIG. 6 is a symbolic view of an X-ray picture similar to FIG. 5 of a breast implant patient utilizing the paddle of the present invention.

For a craniocaudal view mammogram, the patient is standing or sitting with the compression members 14 and 18 horizontally disposed as seen in FIGS. 2 and 3. The patient's breast is inserted between members 14 and 18, and laterally positioned so as to align the cutout 44 directly over the breast implant. The lateral positioning can also be accommodated by releasing bolt 32 and sliding paddle 18 laterally in slot 30. With the cutout 44 properly aligned over the implant, the paddle 18 is brought downward by the transport belt 22 to compress the breast tissue to the desired thickness for the X-ray exposure. By the presence of the cutout 44, no direct pressure is applied to the breast implant which would normally cause it to flatten and enlarge in cross section, as illustrated in FIG. 5. In the presence of cutout 44 the implant 60a, as shown in FIG. 6, has a much less horizontal cross sectional area than seen in FIG. 5 due to the lack of direct compression on the implant. This provides a substantially larger tissue area 52a for the radiologist to examine than the smaller area 52 of the prior art paddles of FIG. 5. With this increased viewing of breast tissue as a result of increased compression and spreading of the breast tissue, as seen in FIG. 6, the radiologist is allowed to take fewer pictures to see the same tissue and decrease the overall radiation exposure to the patient.

The longitudinally extended corners 46 of the paddle give additional width capacity which is sometimes desired in lateral or oblique view pictures, while the remainder of the paddle 18 is smaller in size and less cumbersome. In some lateral views the center of the implant is below the center of the breast and with the cutout 44 centered on the implant there is a need for additional width to compress upper breast tissue.

The invention has been described in detail herein in accordance with certain embodiments, yet many modifications may be made to the technique and use of the cutout paddles without departing from the scope of the invention. It is intended that all matter contained in the above description or shown in the accompanying drawings shall be interpreted as illustrative. Accordingly, it is intended by the appended claims to cover all such modifications and changes which fall within the true spirit and scope of the present invention.

What is claimed is:

1. In a mammography system for patients with breast implants, apparatus for compressing and positioning the breast for penetrating radiation and image formation of internal tissue on X-ray film, the improvement comprising:

a compression paddle means formed of transparent, X-ray transmissive material which is substantially rectangular in shape with extended front corners, the paddle means including a planar bottom having sidewalls extending normally from the bottom surrounding the periphery thereof, an arcuate cutout means in the front edge of the planar bottom shaped to substantially surround while not compressing the breast implant, the front corners of the paddle extending outward from the arcuate cutout so that tissue laterally of the implant can be examined at the same time.

2. In a mammograph system as set forth in claim 1 wherein the arcuate cutout has no sidewall.

3. In a mammograph system as set forth in claim 1 wherein the paddle means is formed of a polycarbonate sheet shaped with no sidewall surrounding the arcuate cutout and the front corners of the paddle are substantially rounded.

4. In a mammograph system as set forth in claim 1 wherein the paddle means is formed of a polycarbonate sheet, with the sidewalls surrounding the periphery thereof except for the arcuate cutout and the front corners of the paddle means are more widely spaced apart than the rear corners.

5. A mammography system for patients with breast implants, apparatus for compressing and positioning the breast for penetrating radiation and image formation of internal tissue on X-ray film, comprising:

a base member;

a radiation source emitting a beam;

a stationary compression member containing a removable film plate connected to the base member;

a linear transport means on the base member;

a compression paddle means attached to the transport means acting in conjunction with the stationary compression member, the paddle means formed of a transparent X-ray transmissive sheet which is substantially rectangular in shape with extended front corners, the paddle means includes a planar bottom having sidewalls extending normally from the bottom surrounding the periphery thereof, an arcuate cutout means in the front edge of the planar bottom shaped to substantially surround while not compressing the breast implant, the front corners of the paddle means extending substantially outward from the cutout so that tissue laterally of the implant can be examined at the same time.

6. In a mammograph system as set forth in claim 5, including a lateral adjustment means on the linear transport which allows the paddle means to be shifted laterally to keep the cutout means positioned over the implant.

* * * * *